United States Patent
McCauley

(10) Patent No.: US 8,131,498 B1
(45) Date of Patent: Mar. 6, 2012

(54) SYSTEMS AND METHODS FOR AN IMPROVED WEIGHT DISTRIBUTION SENSORY DEVICE WITH INTEGRATED CONTROLS

(76) Inventor: Jack J. McCauley, Danville, CA (US)

( * ) Notice: Subject to any disclaimer, the term of this patent is extended or adjusted under 35 U.S.C. 154(b) by 412 days.

(21) Appl. No.: 12/402,178

(22) Filed: Mar. 11, 2009

(51) Int. Cl.
G06F 19/00 (2011.01)
G06F 7/00 (2006.01)
B60K 28/00 (2006.01)

(52) U.S. Cl. .......... 702/139; 701/29; 180/274; 177/144

(58) Field of Classification Search ............ 702/139, 702/141, 173; 701/29, 45; 180/45, 274
See application file for complete search history.

(56) References Cited

U.S. PATENT DOCUMENTS 7,407,029 B2 * 8/2008 Breed et al. ............ 180/274

* cited by examiner

Primary Examiner — Bryan Bui
(74) Attorney, Agent, or Firm — Kang Lim

(57) ABSTRACT

An improved weight distribution sensory device with integrated controls is provided. Such a weight distribution sensory device, often referred to as a balance platform, may include a chassis for supporting a user, pressure sensors and control sensors coupled to the chassis, and a processor. The pressure sensors generate pressure data regarding the compression force from the weight of the user on the chassis. The control sensors are located on a forward dorsal portion of the chassis, and may generate control data when manipulated by the user. The control sensors include at least one proximity sensor which senses object proximity (such as the user's foot) in a narrow band above the sensor along the y-axis. The processor may then receive the pressure data and the control data, and may generate a total weight of the user and a weight distribution of the user, and action data for the user by cross referencing the weight distribution with the control data.

20 Claims, 16 Drawing Sheets

SYSTEMS AND METHODS FOR AN IMPROVED WEIGHT DISTRIBUTION SENSORY DEVICE WITH INTEGRATED CONTROLS

BACKGROUND OF THE INVENTION

The present invention relates to weight distribution sensing for use in gaming, exercise and therapy purposes. More particularly, the present invention relates to a device for sensing weight distribution which integrates an advanced control interface.

Currently, balance platforms utilize the distribution of weight (also known as user balance, or center of gravity) to determine posture and positioning. Such balance platform devices may be coupled to a processing system for analysis and feedback to the user who is standing on the balance platform. The processing system may be a gaming consol, or other computerized program. Balance accuracy, steadiness, and control may be sensed and compiled into feedback statistics for the user. The feedback may including general posture ratings, physical adeptness, body kinetic control, game score and other indices. One notable balance platform on the current market is the Wii Fit™ by Nintendo™.

The current balance platforms suffer from some shortcomings, however. Among these shortcomings is the lack of integrated controls, cost of manufacture, and degree of precision. The current balance platforms often require a separate hand held control device for inputting controls by the user to the game consol or other processor. The reason for this limitation is that, until now, it seemed impracticable to integrate easy-to-use and accurate controls into the balance platform because the user stands on the platform, thereby limiting controls manipulation to the user's foot. Cost and precision limitation of current balance platforms is due to sensor location and engineering design.

Hence there is a need for an improved weight distribution sensory device with integrated interface controls. Such a system may provide an improvement over current balance platforms in both manufacturing costs and sensory accuracy. Additionally, such an improved system may enable user interface without the need for an independent handheld controller. Such a system may enable increased usability in a wider range of applications than current balance platform systems.

SUMMARY OF THE INVENTION

To achieve the foregoing and in accordance with the present invention, an improved weight distribution sensory device with integrated controls is provided. Such a weight distribution sensory device, often referred to as a balance platform, may be useful in conjunction with gaming, exercise, and physical therapy.

Some embodiments of the improved weight distribution sensory system may be useful in conjunction with a user. The improved weight distribution sensory system may include a chassis for supporting the user, more than one pressure sensors coupled to the chassis, one or more control sensors coupled to the chassis, and a processor.

The pressure sensors may generate pressure data regarding the compression force from the weight of the user on the chassis. The control sensors are located on a forward dorsal portion of the chassis, and may generate control data when manipulated by the user. The control sensors may include at least one proximity sensor which senses object proximity (such as the user's foot) in a narrow band above the sensor along the y-axis. The processor may then receive the pressure data and the control data. The processor may then generate a total weight of the user and a weight distribution of the user from the pressure data, and may also generate action data for the user by cross referencing the weight distribution with the control data. For example, an array of proximity sensors may be used to track motion of the user.

The improved weight distribution sensory system may also include an outputter coupled to the processor and a downstream system. The outputter outputs the total weight, the weight distribution, the control data, and the action data to the downstream system. The downstream system may be a computer system or game console system.

The improved weight distribution sensory system may also include an accelerometer to measure accelerations in the chassis. The processor may cross reference the measured accelerations in the chassis when generating the action data.

Note that the various features of the present invention can be practiced alone or in combination. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well-known process steps and/or structures have not been described in detail in order to not unnecessarily obscure the present invention. The features and advantages of the present invention may be better understood with reference to the drawings and discussions that follow.

Figure 1:
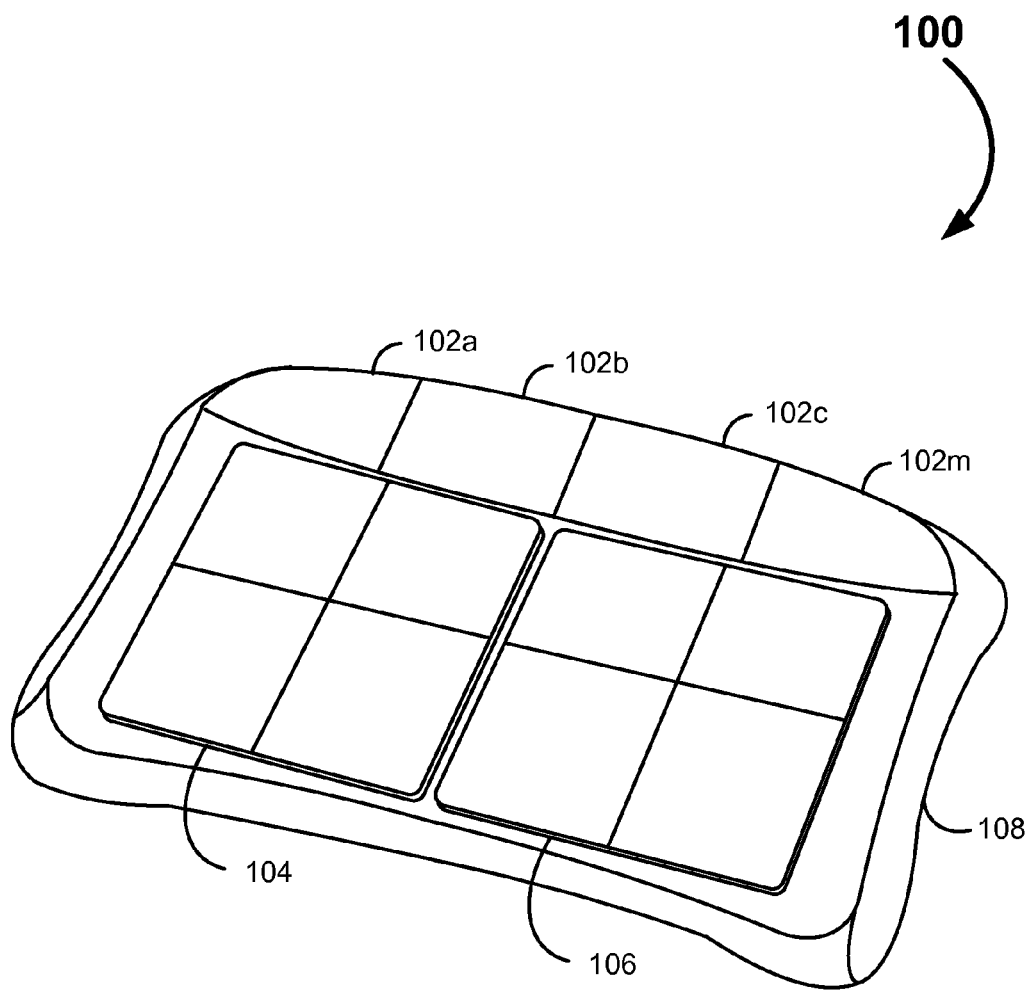
FIG. 1 shows an isometric illustration of an embodiment of an improved weight distribution sensory device with integrated controls in accordance with an embodiment of the present invention.

To facilitate discussion, FIG. 1 shows an isometric illustration of an embodiment of an Improved Weight Distribution Sensory Device with Integrated Controls 100 in accordance with an embodiment of the present invention. In some embodiments, the Improved Weight Distribution Sensory Device with Integrated Controls 100 may be roughly 16 inches wide, 14 inches tall and 2 inches thick; however, any dimensions of the Improved Weight Distribution Sensory Device with Integrated Controls 100 are contemplated by the present invention, dependent upon intended use, cost or other design criteria.

The Improved Weight Distribution Sensory Device with Integrated Controls 100 may include a Chassis 108. The Chassis 108 may be plastic, metal, ceramic, wood, composite, or other suitable material. The Chassis 108 may provide aesthetic appeal and structural support. Additionally, the Chassis 108 may protect internal mechanisms of the Improved Weight Distribution Sensory Device with Integrated Controls 100 from exposure to damage, dust, and user injury.

Lining the front of the Improved Weight Distribution Sensory Device with Integrated Controls 100 there may be one or more Control Pads 102a, 102b to 102m. While four Control Pads 102a, 102b to 102m are illustrated, any number of Control Pads 102a, 102b to 102m is possible. The Control Pads 102a, 102b to 102m may be color coded for ease of differentiation. Ideally, in some embodiments, each of the Control Pads 102a, 102b to 102m may be wide enough to accommodate an average foot thereby limiting the possibility of inputting controls via the wrong Control Pads 102a, 102b to 102m. Each Control Pads 102a, 102b to 102m may include a pressure sensor, proximity sensor, heat sensor, motion sensor or other sensor. Thus, in some embodiments, the user may simply pass her foot over a particular Control Pads 102a, 102b to 102m in order to provide control input into the Improved Weight Distribution Sensory Device with Integrated Controls 100. In addition to enabling ease of control, this feature enables advanced gaming and exercise options including soccer and foot tracking.

The Improved Weight Distribution Sensory Device with Integrated Controls 100 may also include a Left Foot Pad 104 and a Right Foot Pad 106. The user will typically stand on the Left Foot Pad 104 and Right Foot Pad 106 such that her feet are centered on the Left Foot Pad 104 and Right Foot Pad 106. The Left Foot Pad 104 and Right Foot Pad 106 may include crosshair-like visual indications to aid the user in placing her feet properly upon the Left Foot Pad 104 and Right Foot Pad 106 respectively. In some embodiments, the Left Foot Pad 104 and Right Foot Pad 106 may be independent pads from the Chassis 108, each including independent weight distribution sensors. Such embodiments may enable greater accuracy in determining user posture and stance of the user. In some alternate embodiments, the Left Foot Pad 104 and Right Foot Pad 106 may be fused or even a single unit with the Chassis 108. In such embodiments, the weight sensors may be located on the bottom of the Chassis 108. This enables fewer sensors to be used, but may loose some of the foot specific data available when the Left Foot Pad 104 and Right Foot Pad 106 are independent.

Figure 2:
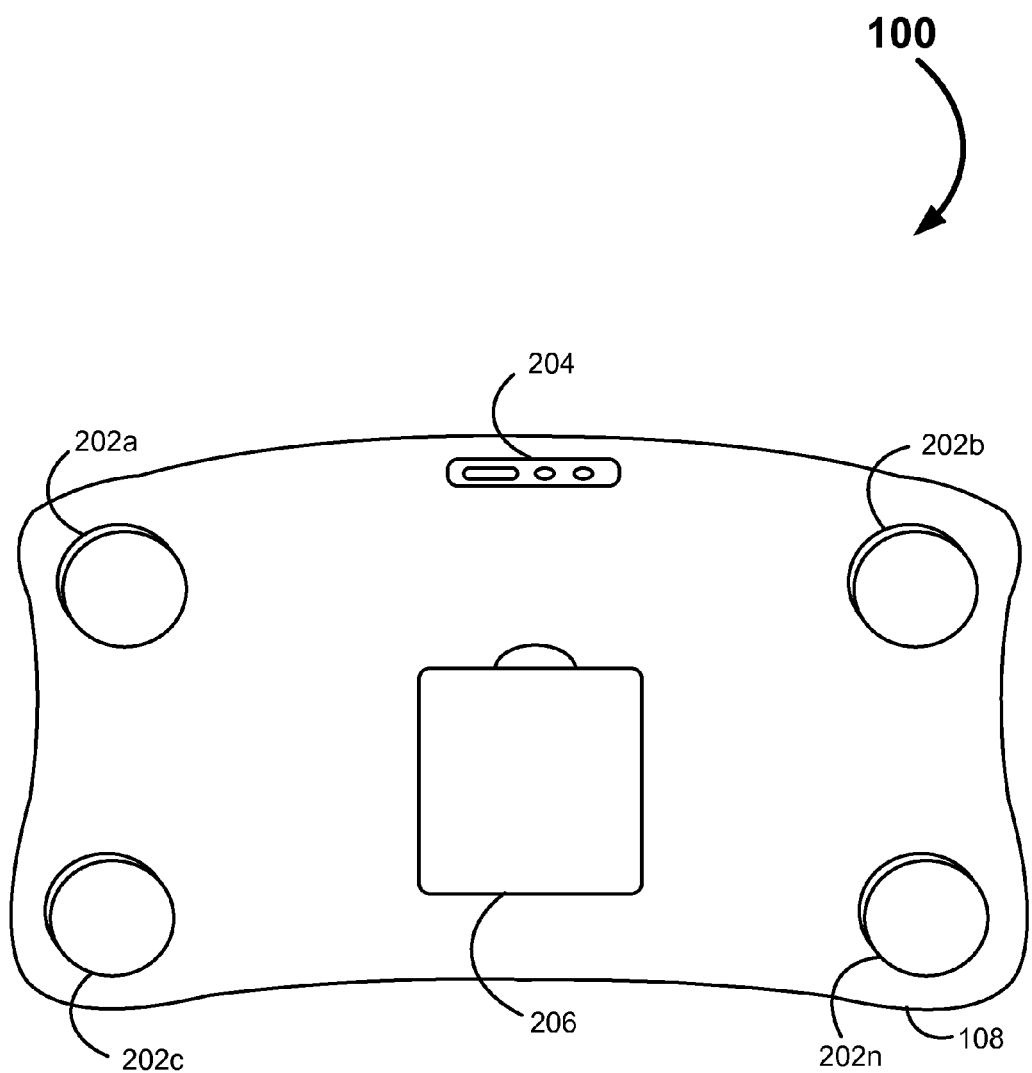
FIG. 2 shows a bottom view illustration of an embodiment of the improved weight distribution sensory device with integrated controls in accordance with an embodiment of the present invention.

FIG. 2 shows a bottom view illustration of an embodiment of the Improved Weight Distribution Sensory Device with Integrated Controls 100. One or more Platform Feet 202a, 202b to 202n may be seen on the bottom of the Improved Weight Distribution Sensory Device with Integrated Controls 100. In this exemplary illustration, four Platform Feet 202a, 202b to 202n are shown. In some embodiments, the Platform Feet 202a, 202b to 202n may include pressure or weight sensors. The pressure measured by each of the sensors in each Platform Feet 202a, 202b to 202n may be combined to generate the total load (user weight) as well as the center of balance for the user. For accurate determination of the center of balance, a total of at least three Platform Feet 202a, 202b to 202n may be used.

The weight sensors may include resistive load sensors, beam load sensors, strain gauges, and spring load sensors. Additionally, piezo compressive load sensors may be used.

A Battery Pack 206 may also be seen on the bottom of the Improved Weight Distribution Sensory Device with Integrated Controls 100. In some embodiments, where the Improved Weight Distribution Sensory Device with Integrated Controls 100 is wired to a processor system, such as a game consol, there may be no need for batteries as there is external power available. However, for wireless versions of the Improved Weight Distribution Sensory Device 100, a Battery Pack 206 is typically needed.

Additionally, the Improved Weight Distribution Sensory Device 100 may have a Manual Interface 204. The Manual Interface 204 may include one or more buttons, such as a synchronization button and a power button. The Manual Interface 204 may likewise include a Universal Serial Bus (USB) port, or other access port, for coupling the Improved Weight Distribution Sensory Device 100 via a wire to a processor system. In addition, the Manual Interface 204 may include a transmitter, or in some embodiments, a transceiver, for sending data to the downstream system. Of course, the Manual Interface 204 may include more or fewer functions as is desired.

Figure 3:
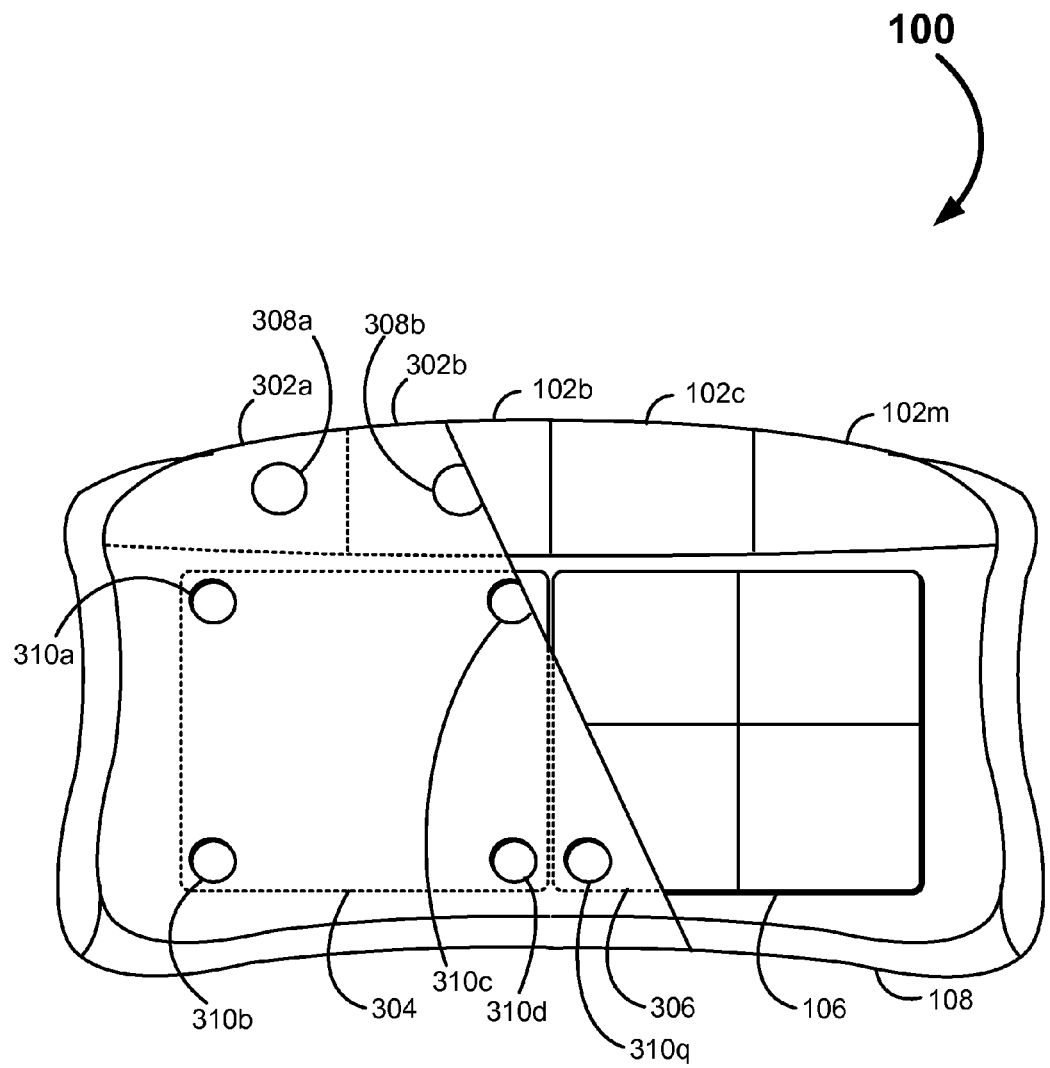
FIG. 3 shows a top partial cutaway view illustration of an embodiment of the improved weight distribution sensory device with integrated controls in accordance with an embodiment of the present invention.

FIG. 3 shows a top partial-cutaway view illustration of an embodiment of the Improved Weight Distribution Sensory Device with Integrated Controls 100. The left side of the illustration has been cut away to illustrate under workings of the Improved Weight Distribution Sensory Device 100. For example, the Control Pads 102a, 102b to 102m may be seen, and underneath each of the Control Pads 102a, 102b to 102m may be a respective Control Sensor 308a, 308b to 308m. The Control Sensor 308a, 308b to 308m may include, but is not limited to, heat, motion, touch or proximity sensors. In some embodiments, proximity sensors may be used with a narrow column of measured area extending approximately 10 to 14 inches above the sensor. Thus, if the user kicks, or moves her foot, over the sensor it may be registered as an input. Likewise, foot position in balancing, kicks and foot sweeps may be sensed by the Control Sensors 308a, 308b to 308m. Foot speed and motion may likewise be tracked by the Control Sensors 308a, 308b to 308m when the foot passes over multiple sensors.

Additionally, the Left Foot Pad 104 and Right Foot Pad 106 may sit in a Left Pad Bed 304 and Right Pad Bed 306, respectively. In some embodiments, the Left Foot Pad 104 and Right Foot Pad 106 may be supported by more than one 310. There are eight Pressure Sensors 310a, 310b to 310q in the present illustration. Thus, each of the Left Foot Pad 104 and Right Foot Pad 106 may be independently supported by Pressure Sensors 310a, 310b to 310q. Thus, weight distributions on each foot pad may be analyzed separately. In some alternate embodiments, the Left Foot Pad 104 and Right Foot Pad 106 may be a single foot pad. In these embodiments fewer Pressure Sensors 310a, 310b to 310q may be utilized. As with the embodiments where the weight sensors are located in the Platform Feet 202a, 202b to 202n, the Pressure Sensors 310a, 310b to 310q may include any of resistive load sensors, beam load sensors, strain gauges, and spring load sensors. Additionally, piezo compressive load sensors may be used.

Figure 4:
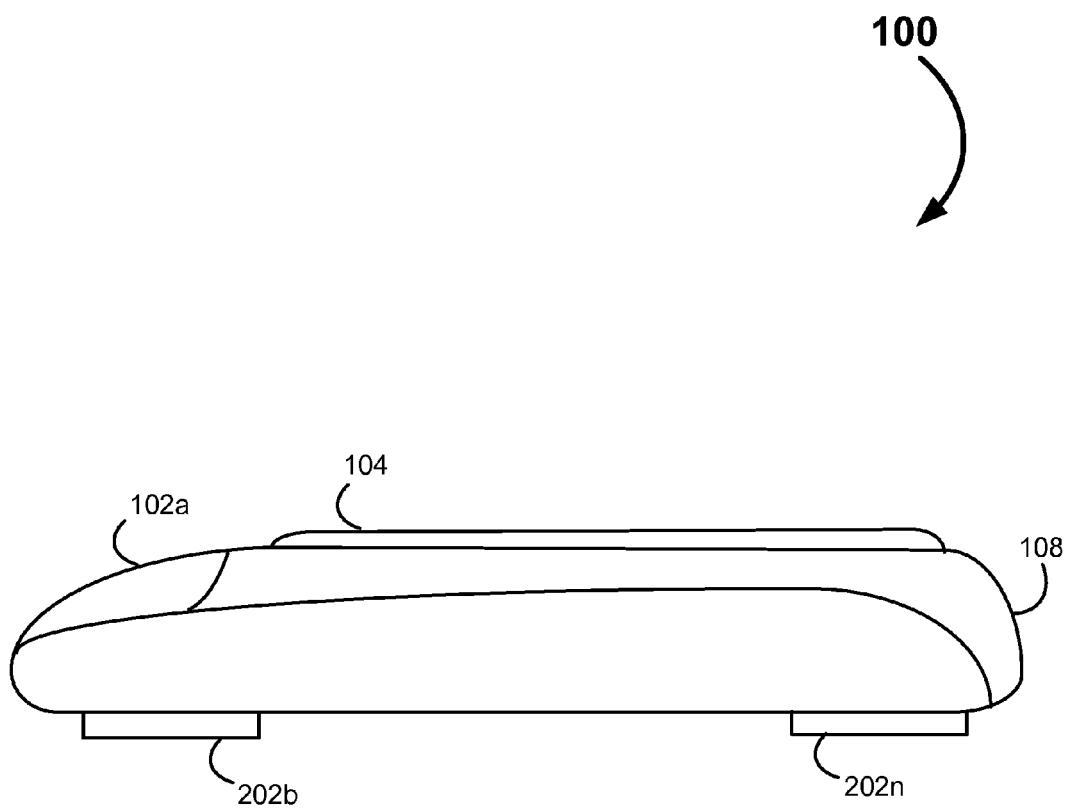
FIG. 4 shows a side view illustration of an embodiment of the improved weight distribution sensory device with integrated controls in accordance with an embodiment of the present invention.

FIG. 4 shows a side view illustration of an embodiment of the Improved Weight Distribution Sensory Device with Integrated Controls 100. Again, the Control Pads 102a, 102b to 102m may be seen on the forward portion of the Improved Weight Distribution Sensory Device with Integrated Controls 100. The Platform Feet 202a, 202b to 202n supports the Chassis 108, and the Left Foot Pad 104 may be mounted on top of the Chassis 108. This illustration is offered to provide a clearer understanding of the geometry of the Improved Weight Distribution Sensory Device 100.

Figure 5A:
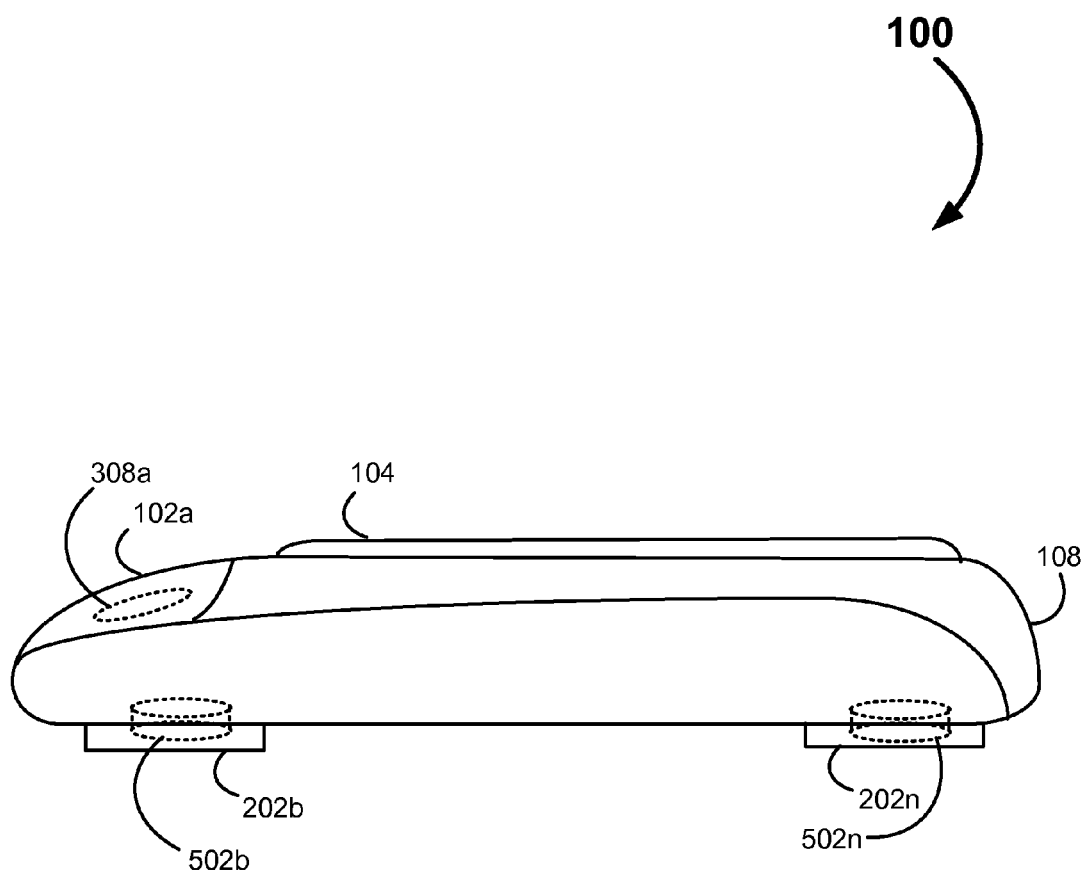
FIG. 5A shows a cutaway side view illustration of a first embodiment of the improved weight distribution sensory device with integrated controls in accordance with an embodiment of the present invention.

FIG. 5A shows a cutaway side view illustration of a first embodiment of the Improved Weight Distribution Sensory Device with Integrated Controls 100. Again, the Control Pads 102a, 102b to 102m may be seen on the forward portion of the Improved Weight Distribution Sensory Device 100. The Platform Feet 202a, 202b to 202n supports the Chassis 108, and the Left Foot Pad 104 may be mounted on top of the Chassis 108. In addition the Control Sensors 308a, 308b to 308m may be seen existing beneath the Control Pads 102a, 102b to 102m. The Control Sensors 308a, 308b to 308m may, in some embodiments, sense object proximity in a narrow column extending along the y-axis to a height of 10-14 inches. Of course, wider or narrower proximity beams may be used. Additionally, height of proximity sensation may likewise be altered to virtually any height dependent upon desired application. Thus, for some embodiments, the proximity sensors may be viable to a height as to be capable of determining hand and arm position. Additionally, in some embodiments, more Control Sensors 308a, 308b to 308m may be utilized to provide triangulation of the proximate object, thereby providing a greater level of detail as to the object's, be it a foot or hand, location. Likewise, by tracking object proximity across multiple Control Sensors 308a, 308b to 308m the object's motion may be determined.

In this embodiment Bottom Pressure Sensors 502a, 502b to 502n may be seen existing in the Platform Feet 202a, 202b to 202n. As previously discussed, these sensors may provide weight distribution information for the entire balance platform; however, weight distribution for each individual foot of the user may be limited. Again, such sensors may include resistive load sensors, beam load sensors, strain gauges, spring load sensors, and piezo compressive load sensors.

Figure 5B:
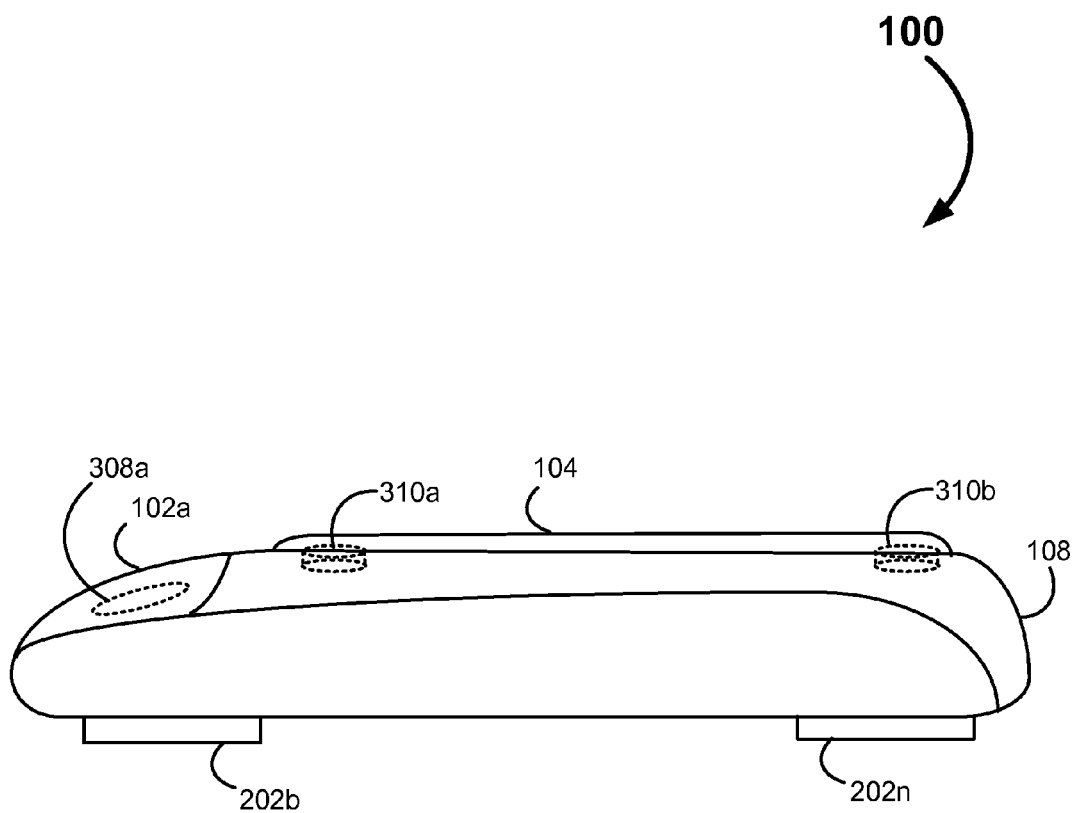
FIG. 5B shows a cutaway side view illustration of a second embodiment of the improved weight distribution sensory device with integrated controls in accordance with an embodiment of the present invention.

FIG. 5B shows a cutaway side view illustration of a second embodiment of the Improved Weight Distribution Sensory Device with Integrated Controls 100. Again, the Control Pads 102a, 102b to 102m may be seen on the forward portion of the Improved Weight Distribution Sensory Device 100. The Platform Feet 202a, 202b to 202n supports the Chassis 108, and the Left Foot Pad 104 may be mounted on top of the Chassis 108. In addition the Control Sensor 308a, 308b to 308m may be seen existing beneath the Control Pads 102a, 102b to 102m. The Control Sensor 308a, 308b to 308m may, in some embodiments, sense object proximity in a narrow column extending along the y-axis as discussed above.

In this embodiment the Pressure Sensors 310a, 310b to 310q may be seen existing in between the Left Foot Pad 104 and Chassis 108. As previously discussed, these sensors may provide weight distribution information for each of the Left Foot Pad 104 and Right Foot Pad 106 independently, or if desired, the Left Foot Pad 104 and Right Foot Pad 106 may be fused and the Pressure Sensors 310a, 310b to 310q may provide weight distribution for the entire foot pad formed by the fused Left Foot Pad 104 and Right Foot Pad 106. Again, the Pressure Sensors 310a, 310b to 310q may include resistive load sensors, beam load sensors, strain gauges, spring load sensors, and piezo compressive load sensors.

Figure 6A:
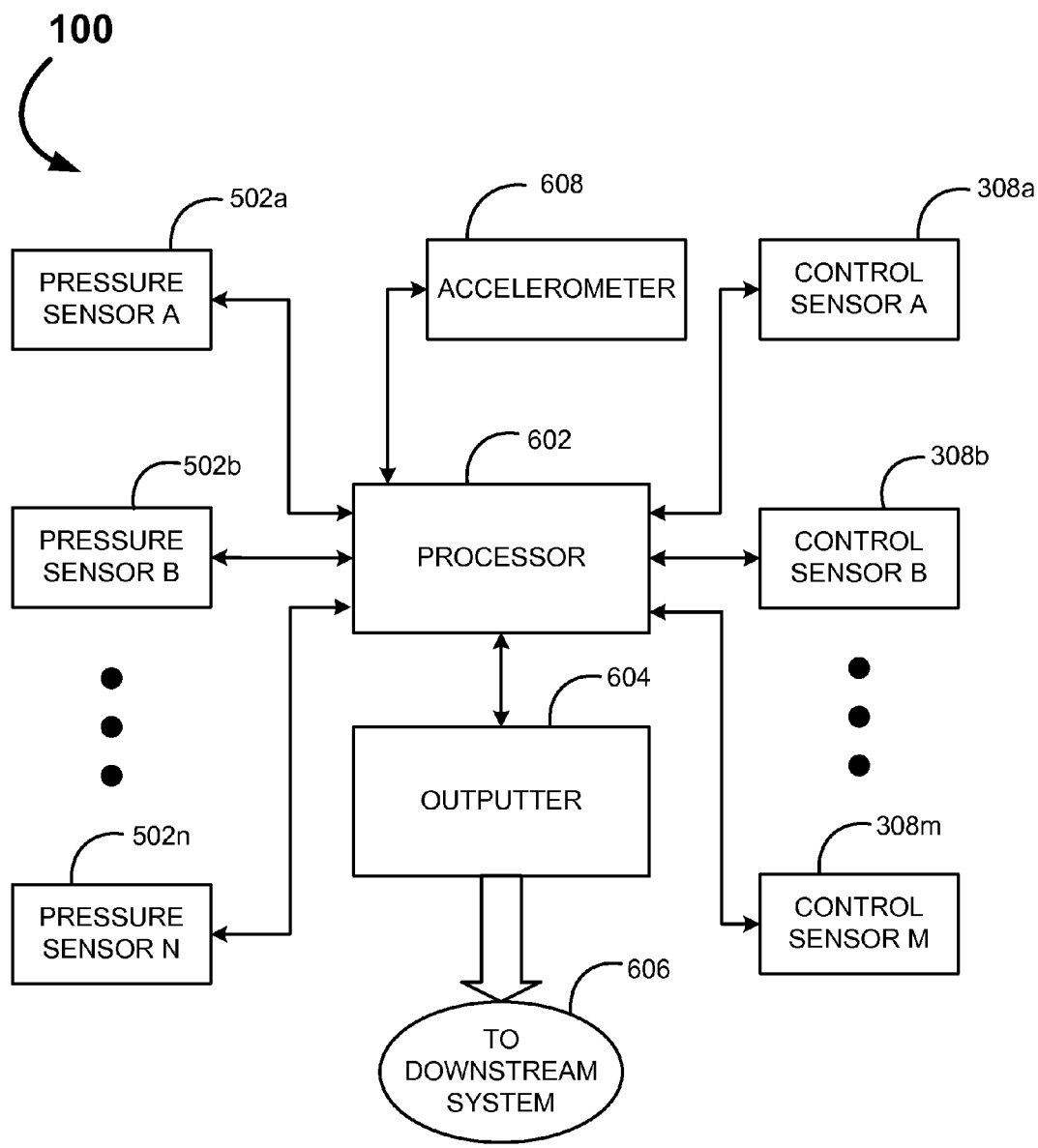
FIG. 6A illustrates a first embodiment of a block diagram for the improved weight distribution sensory device with integrated controls in accordance with an embodiment of the present invention.

FIG. 6A illustrates a first embodiment of a block diagram for the Improved Weight Distribution Sensory Device with Integrated Controls 100. This particular embodiment may be useful when the sensors are found in the Platform Feet 202a, 202b to 202n as seen in FIG. 5A. Here measured pressure, or load, from the Bottom Pressure Sensors 502a, 502b to 502n may be provided to a Processor 602. Again, any number of Bottom Pressure Sensors 502a, 502b to 502n may be utilized; however, a minimum of three Bottom Pressure Sensors 502a, 502b to 502n are typically required to generate a reliable weight distribution. The Processor 602 may likewise receive inputs from the Control Sensors 308a, 308b to 308m and one or more Accelerometer 608. The Processor 602 may include dedicated hardware, software, or a combination for the two, within the Improved Weight Distribution Sensory Device 100.

As discussed previously, the Control Sensors 308a, 308b to 308m may include any number of sensor types, including, but not limited to, proximity sensors, heat sensors, touch sensors and motion sensors. Not previously illustrated, one or more Accelerometer 608 may provide acceleration data to the Processor 602. Such acceleration data may indicate sudden impacts, such as the user jumping, or movement of the Improved Weight Distribution Sensory Device 100.

The Processor 602 may process all relevant data to generate control and weight distribution data. This data may be provided to an Outputter 604 which may generate an output to a downstream system at 606. The downstream system may include a gaming console, a computer or other processing device.

In some embodiments, there may be no downstream system. In such embodiments, the Improved Weight Distribution Sensory Device with Integrated Controls 100 may couple directly with a video device, such as a monitor or television. However, if the Improved Weight Distribution Sensory Device 100 does couple to a downstream system, such as a gaming console, the system may couple to a video device separately. Additionally, the Processor 602 may, in some embodiments, be emulative software on the downstream system.

Figure 6B:
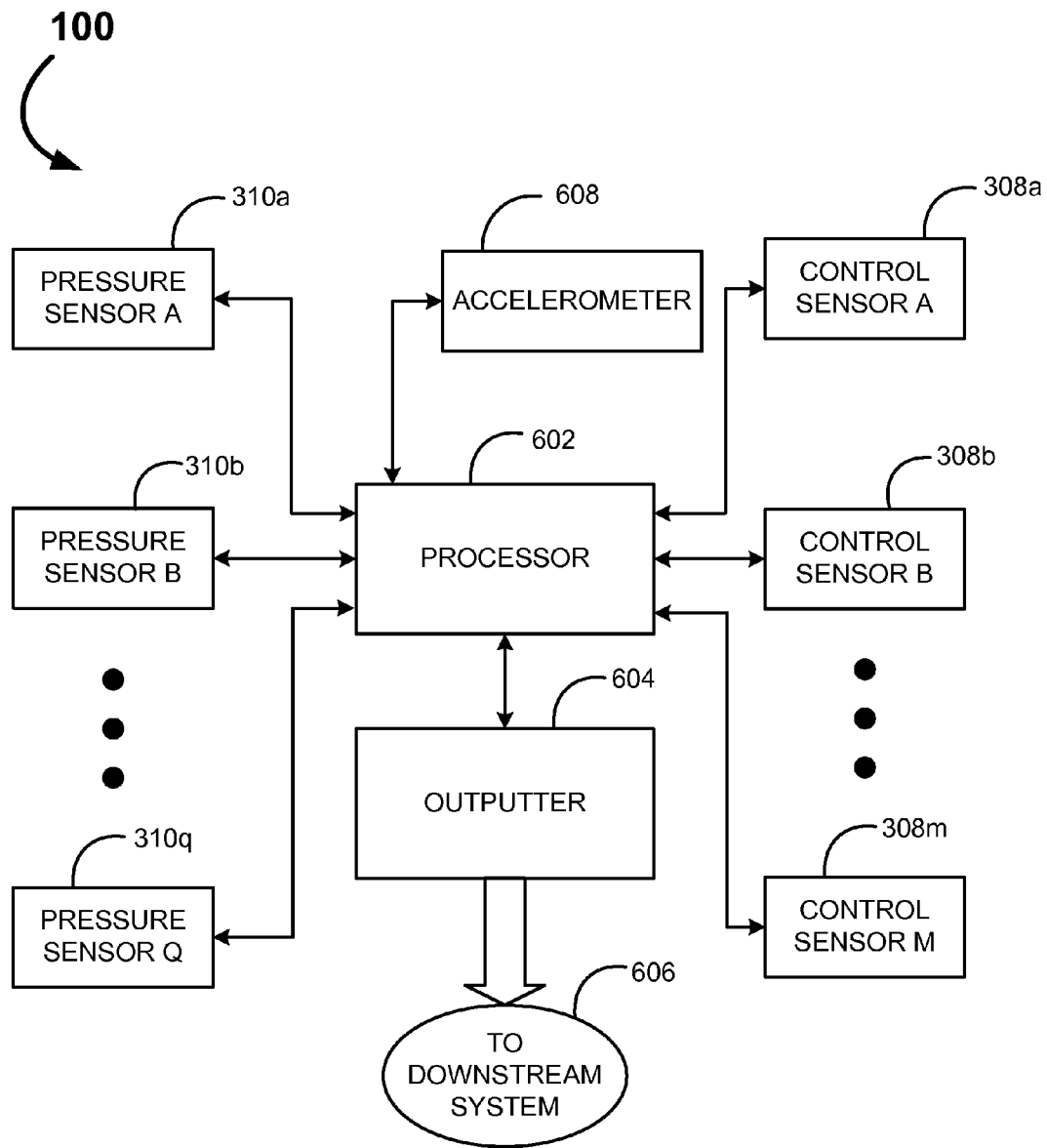
FIG. 6B illustrates a second embodiment of a block diagram for the improved weight distribution sensory device with integrated controls in accordance with an embodiment of the present invention.

FIG. 6B illustrates a second embodiment of a block diagram for the Improved Weight Distribution Sensory Device with Integrated Controls 100. This particular embodiment may be useful when the sensors are found between the Chassis 108 and the Left Foot Pad 104 and Right Foot Pad 106, as seen in FIG. 5B. Here measured pressure, or load, from the Pressure Sensors 310a, 310b to 310q may be provided to the Processor 602. Again, any number of Pressure Sensors 310a, 310b to 310q may be utilized; however, a minimum of three to six Pressure Sensors 310a, 310b to 310q are typically required to generate a reliable weight distribution, dependent upon if the Left Foot Pad 104 and Right Foot Pad 106 are fused or separate. The Processor 602 may likewise receive inputs from the Control Sensors 308a, 308b to 308m and one or more Accelerometer 608. The Processor 602 may include dedicated hardware, software, or a combination for the two, within the Improved Weight Distribution Sensory Device 100.

As discussed previously, the Control Sensors 308a, 308b to 308m may include any number of sensor types, including, but not limited to, proximity sensors, heat sensors, touch sensors and motion sensors. Not previously illustrated, one or more Accelerometer 608 may provide acceleration data to the Processor 602. Such acceleration data may indicate sudden impacts, such as the user jumping, or movement of the Improved Weight Distribution Sensory Device 100.

The Processor 602 may process all relevant data to generate control and weight distribution data. This data may be provided to an Outputter 604 which may generate an output to a downstream system at 606. The downstream system may include a gaming console, a computer or other processing device.

In some embodiments, there may be no downstream system. In such embodiments, the Improved Weight Distribution Sensory Device 100 may couple directly with a video device, such as a monitor or television. However, if the Improved Weight Distribution Sensory Device 100 does couple to a downstream system, such as a gaming console, the system may couple to a video device separately. Additionally, the Processor 602 may, in some embodiments, be emulative software on the downstream system.

Figure 7:
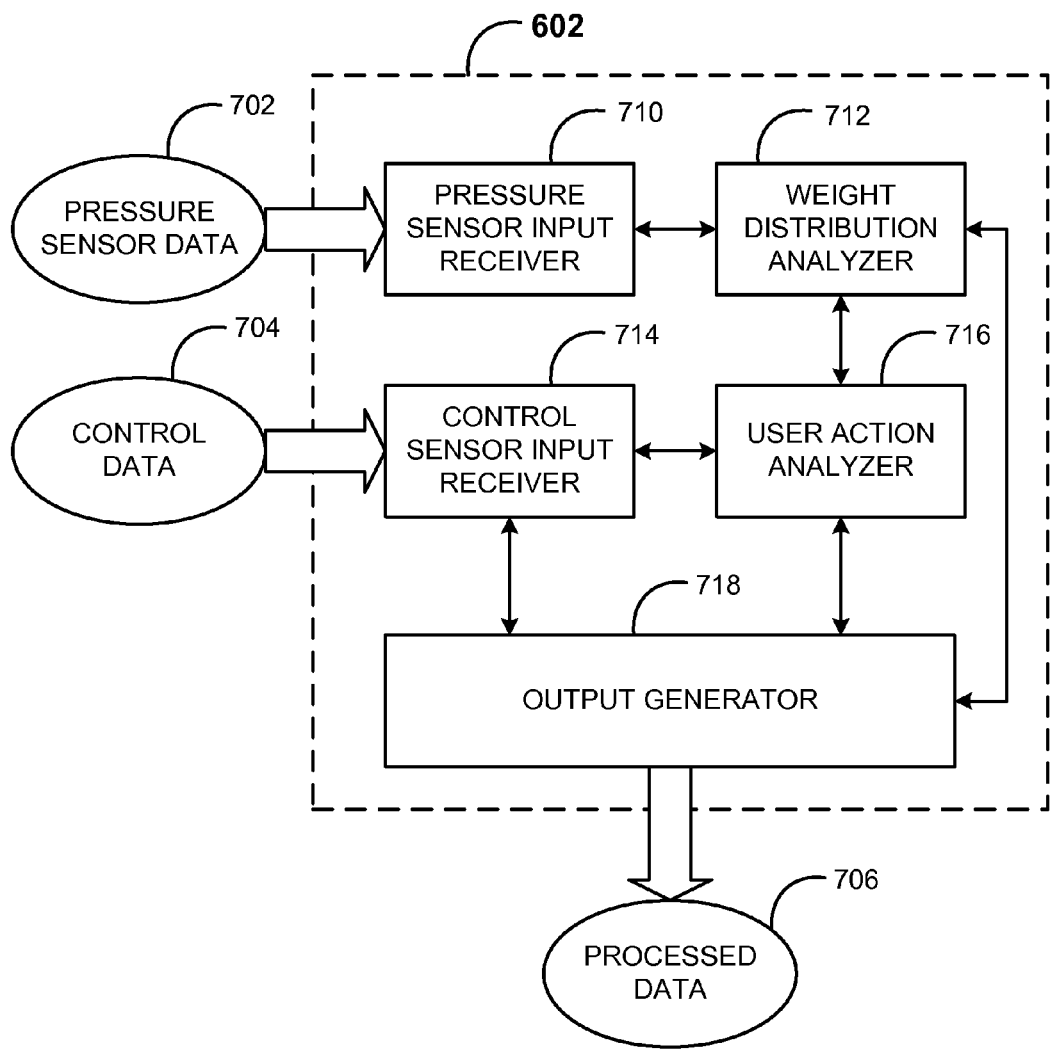
FIG. 7 illustrates an embodiment of a block diagram for the processor for an embodiment of the improved weight distribution sensory device with integrated controls in accordance with an embodiment of the present invention.

FIG. 7 illustrates an embodiment of a block diagram for the Processor 602 of the Improved Weight Distribution Sensory Device with Integrated Controls 100. The Processor 602 may receive pressure sensor data, shown at 702, and control data, shown at 704. The Processor 602 may include, but is not limited to, a Pressure Sensor Input Receiver 710, a Weight Distribution Analyzer 712, a Control Sensor Input Receiver 714, a User Action Analyzer 716 and an Output Generator 718.

The Pressure Sensor Input Receiver 710 may receive the pressure sensor data. The Pressure Sensor Input Receiver 710 may couple to the Weight Distribution Analyzer 712. The Weight Distribution Analyzer 712 may analyze the pressure data to determine weight distribution, including total weight on the Improved Weight Distribution Sensory Device 100 and the center of gravity of the applied weight.

The Control Sensor Input Receiver 714 may receive the control data, and may analyze the control data for motion. The User Action Analyzer 716 may couple to each of the Weight Distribution Analyzer 712 and Control Sensor Input Receiver 714. The weight distribution and control data may be cross referenced to indicate user actions. Thus a shift in center of balance to the right and an input on a left sided control sensor may indicate the user raising her left foot. Additionally, this analysis may be performed in context of the activity the user is engaged in. Thus, if the user is engaged in, for example, a yoga program, and is supposed to be holding a particular pose, the User Action Analyzer 716 may map the balance and control sensor data onto the intended yoga position. Likewise, if the user is engaged in a soccer type game, the User Action Analyzer 716 may be primed for identifying actions such as running in place, kicking and dribbling.

The Output Generator 718 may receive outputs from the Weight Distribution Analyzer 712, the Control Sensor Input Receiver 714 and User Action Analyzer 716 and generate an output of processed data, as shown at 706.

Figure 8:
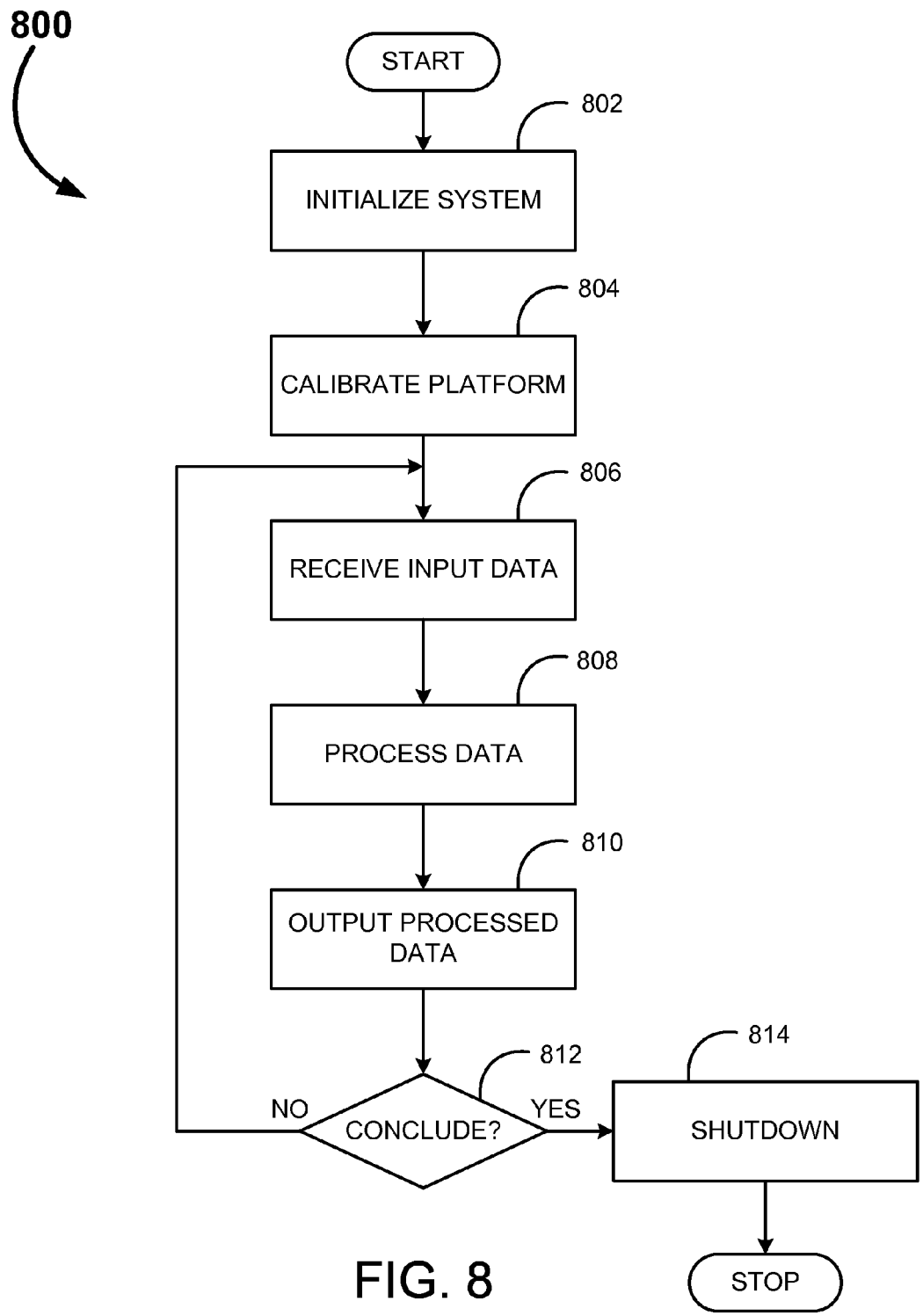
FIG. 8 illustrates an exemplary flow diagram outlining the functioning of the improved weight distribution sensory device with integrated controls in accordance with an embodiment of the present invention.

FIG. 8 illustrates an exemplary flow diagram outlining the functioning of the Improved Weight Distribution Sensory Device with Integrated Controls 100, shown generally at 800. The process begins and then progresses to step 802 where the Improved Weight Distribution Sensory Device 100 is initialized. After initialization, the process then progresses to step 804 where the Improved Weight Distribution Sensory Device 100 is calibrated. Input data is then received at step 806. This received data may include balance (weight distribution) data, as well as control data. Additionally, accelerometer data may be received in some embodiments.

The received data may then be processed at step 808. The process then progresses to step 810 where the processed data is outputted. Such output may be to a downstream system, such as a computer or gaming console, or may be to a display output. The process then progresses to step 812 where an inquiry is made as to whether to conclude the session. If conclusion is desired, the system may undergo a shutdown at step 814. Shutdown may be a power-off, or may include a low-power mode such as sleep or hibernation modes. The process may then end.

Else, if at step 812, concluding the session is not desired, the process then progresses to step 806 where more data is input. The cycle then continues with data analysis and output until it is decided that the session is over.

Figure 9:
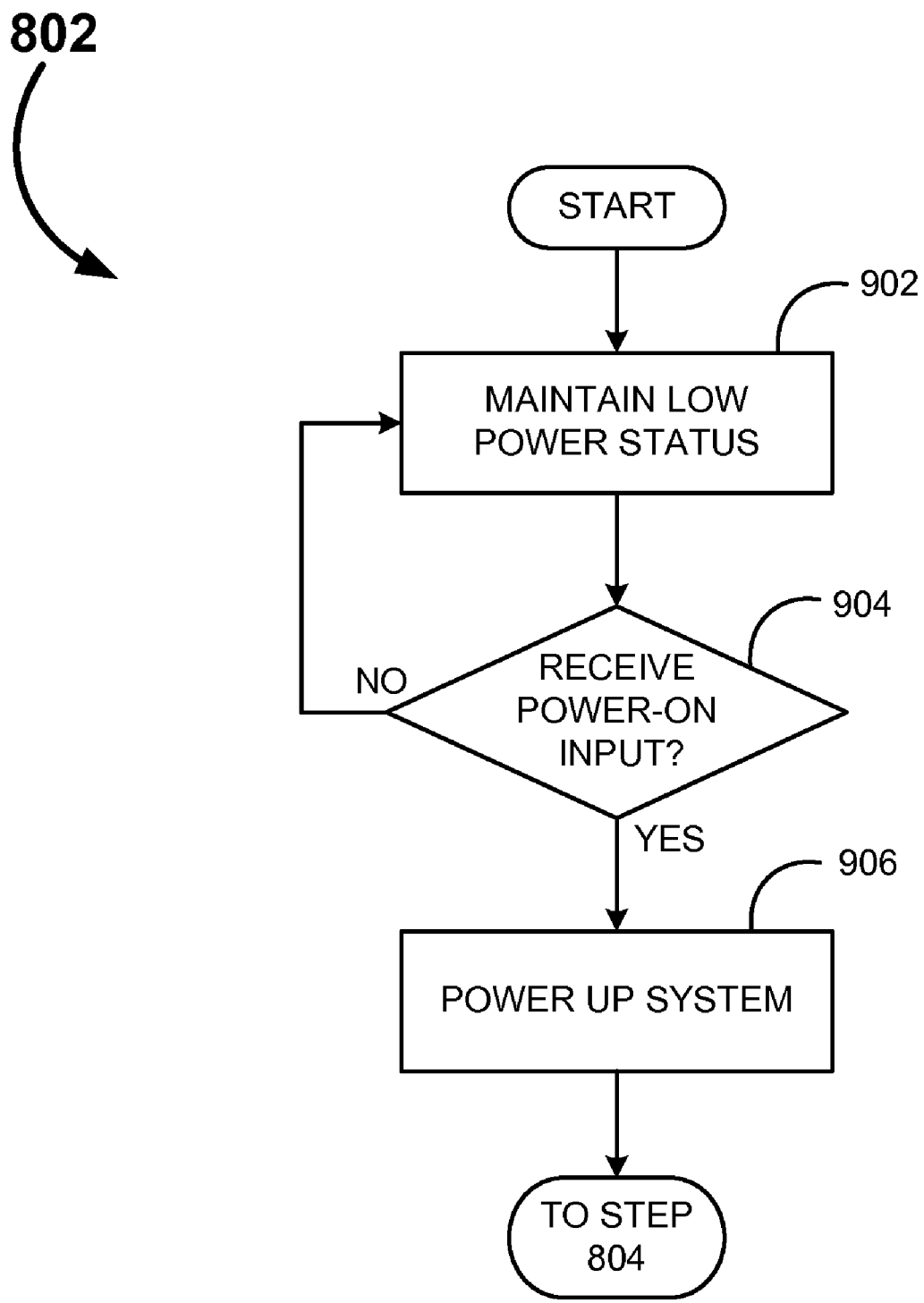
FIG. 9 illustrates an exemplary flow diagram for the initialization of the improved weight distribution sensory device with integrated controls in accordance with an embodiment of the present invention.

FIG. 9 illustrates an exemplary flow diagram for the initialization of the Improved Weight Distribution Sensory Device with Integrated Controls 100, shown generally at 802. The process begins and then progresses to step 902 where a low power status is maintained. The process then progresses to step 904 where an inquiry is made as to whether a power-on input has been received. If such an input is not received, the process goes back to step 902 where the low power status is still maintained.

Else, if there is a received power-on input at step 904, then the process progresses to step 906 where the system is powered up. The process then concludes by progressing to step 804 of FIG. 8.

Figure 10:
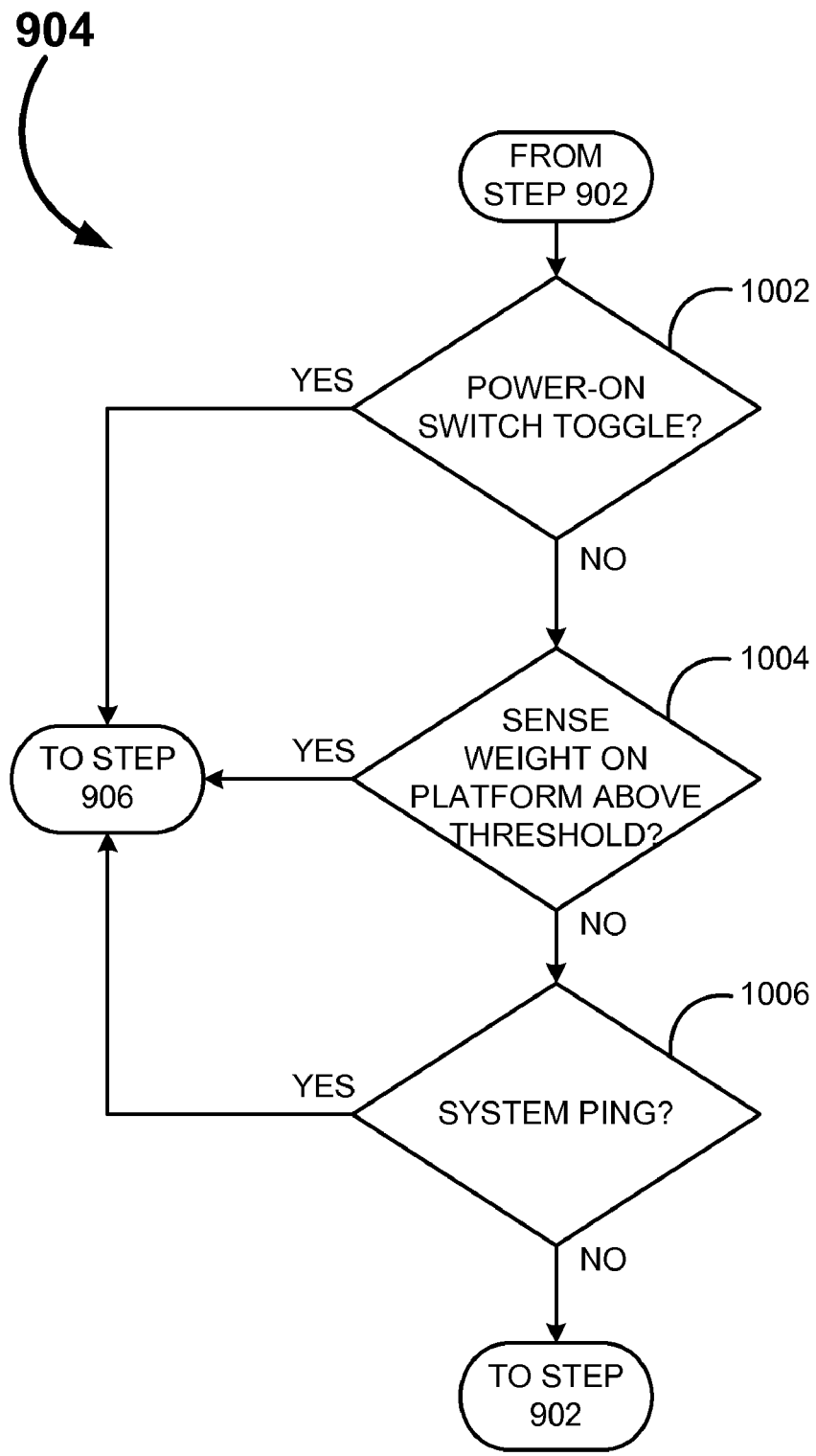
FIG. 10 illustrates an exemplary flow diagram for the receipt of a power-on input for the improved weight distribution sensory device with integrated controls in accordance with an embodiment of the present invention.

FIG. 10 illustrates an exemplary flow diagram for the receipt of a power-on input for the Improved Weight Distribution Sensory Device 100, shown generally at 904. The process begins from step 902 of FIG. 9. The process then progresses to step 1002 where an inquiry is made as to whether the power-on button, or switch, has been toggled.

This may occur if the user manually presses an on-switch. If the power-on-switch is toggled, the process then concludes by progressing to step 906 of FIG. 9.

Else, if at step 1002 the power-on switch is not toggled, the process then progresses to step 1004 where an inquiry is made as to whether there is a weight sensed upon the platform above a particular threshold. This measurement may rely upon acceleration data of the accelerometer, or may rely upon data from the pressure sensors. The threshold may be set so that small bumps or movements of the Improved Weight Distribution Sensory Device 100 do not trigger a power-on; however, large movements or stepping on the Improved Weight Distribution Sensory Device 100 may begin the initialization process. If weight is sensed at step 1004, the process then concludes by progressing to step 906 of FIG. 9.

Otherwise, if at step 1004 no weight above the threshold is detected, the process then progresses to step 1006 where an inquiry is made as to whether the downstream system pings the Improved Weight Distribution Sensory Device with Integrated Controls 100. In some embodiments, when a particular game or program utilizing the Improved Weight Distribution Sensory Device 100 is booted upon the downstream system, be it a gaming console or computer, that system may reach out to the Improved Weight Distribution Sensory Device 100. Such a ping may cause the Improved Weight Distribution Sensory Device 100 to initialize. Thus, if a ping is received, the process then concludes by progressing to step 906 of FIG. 9.

Else, if there is no system ping at step 1006, then there has been no power-on indicator and the process then concludes by progressing to step 902 of FIG. 9 where low power status is maintained.

Figure 11:
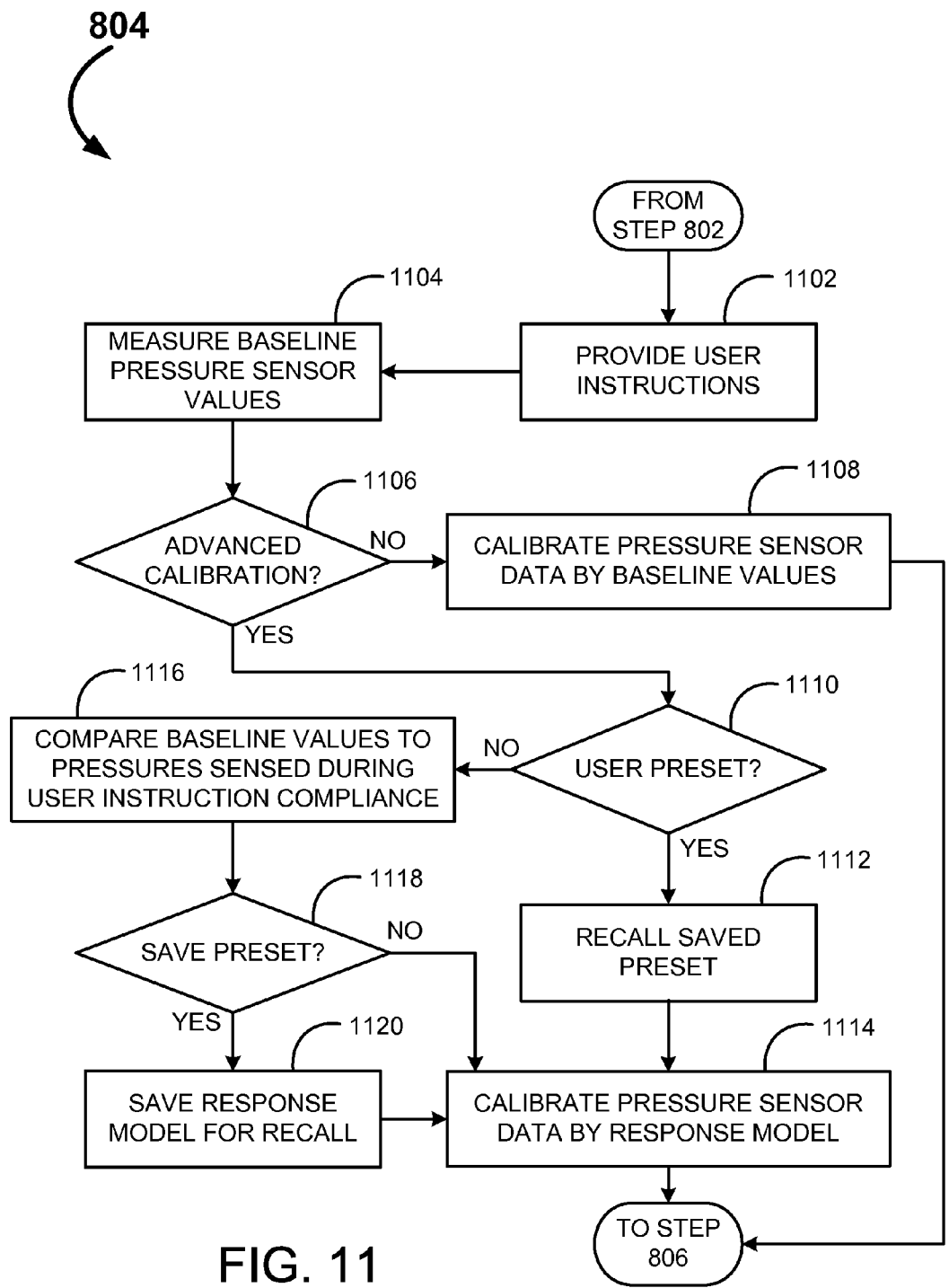
FIG. 11 illustrates an exemplary flow diagram for the calibration of the improved weight distribution sensory device with integrated controls in accordance with an embodiment of the present invention.

FIG. 11 illustrates an exemplary flow diagram for the calibration of the Improved Weight Distribution Sensory Device 100, shown generally at 804. Proper calibration of the Improved Weight Distribution Sensory Device 100 may be required to generate an accurate weight distribution measurement. The process begins from step 802 of FIG. 8. The process then progresses to step to 1102 where the user is provided with instructions. These instructions will typically require the user to get off of the Improved Weight Distribution Sensory Device 100 and then get back on. In some embodiments, these instructions may be more complex: including standing on one foot, jumping or leaning some direction.

While the user is off of the Improved Weight Distribution Sensory Device 100, the baseline pressure sensor value may be measured at step 1104. The process then progresses to step 1106 where an inquiry is made as to whether an advanced calibration is desired. An advanced calibration may provide more accurate measures of weight distribution, but may likewise require more user input. If no advanced calibration is desired, the process then progresses to step 1108 where a basic calibration is done by subtracting the measured baseline pressure sensor values from all later measured pressure sensor values. The process then concludes by progressing to step 806 of FIG. 8.

Else, if an advanced calibration is desired at step 1106, the process then progresses to step 1110 where an inquiry is made as to whether user preset is available. A user preset may be a saved calibration model from a previous advanced calibration. If such a user preset is available, it may be recalled at step 1112. This recalled response model may then be used to calibrate pressure sensor data, at step 1114. The process then concludes by progressing to step 806 of FIG. 8.

Otherwise, if at step 1110 no preset is available, the process then progresses to step 1116 where the baseline values, measured above at step 1104, are compared to pressure sensor readings sensed while the user follows the instructions that were provided at step 1102. This comparison may be used to generate a response model. Then, at step 1118, where an inquiry is made as to whether to save the response model as a user preset. If saving is desired, the response model is saved for recall at step 1120. Then, the process progresses to step 1114 where the response model may then be used to calibrate pressure sensor data. The process then concludes by progressing to step 806 of FIG. 8.

Else, if the response model is not saved at step 1118, the process then progresses to step 1114 where the response model may then be used to calibrate pressure sensor data. The process then concludes by progressing to step 806 of FIG. 8.

Figure 12:
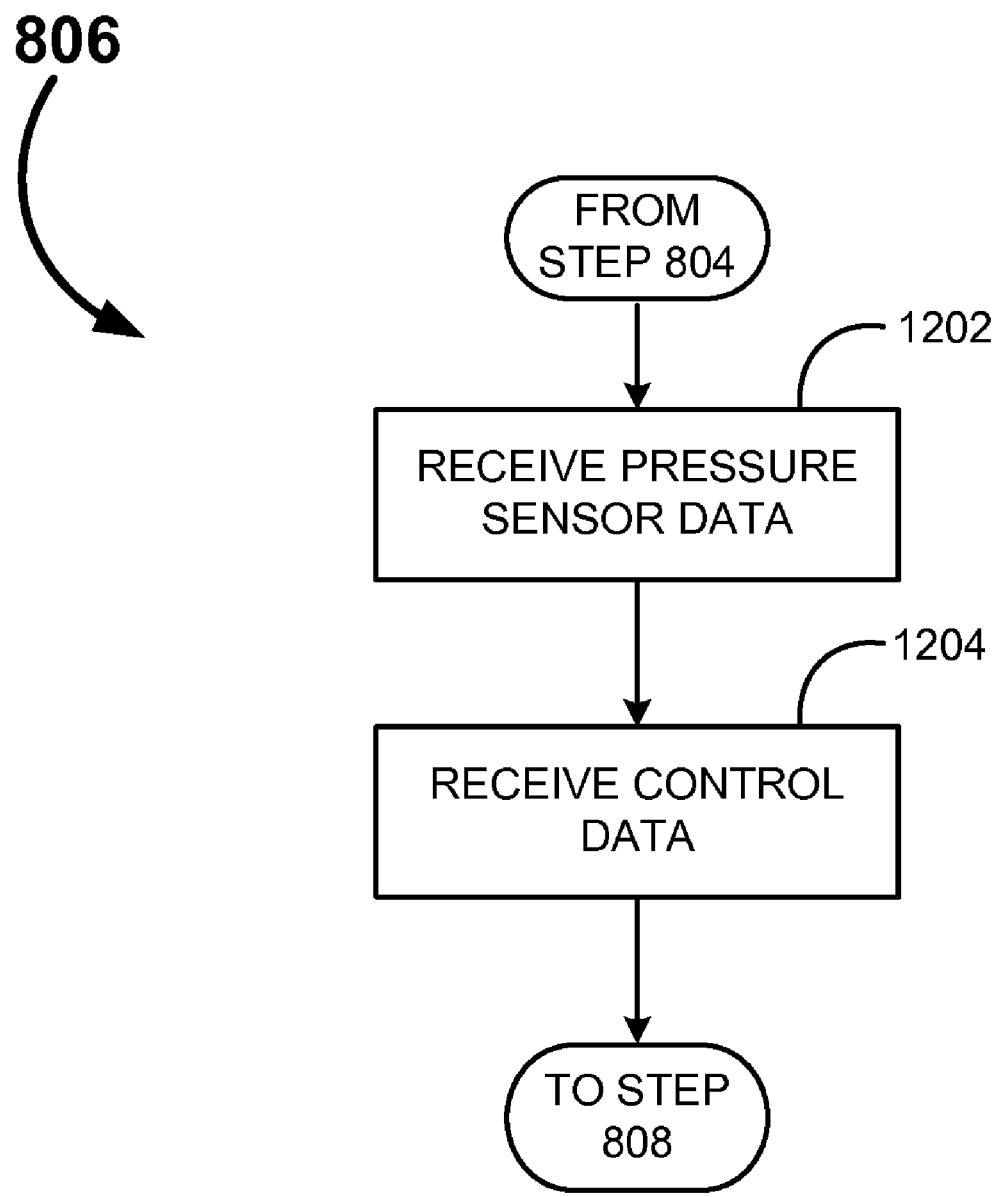
FIG. 12 illustrates an exemplary flow diagram for the receipt of input data for the improved weight distribution sensory device with integrated controls in accordance with an embodiment of the present invention.

FIG. 12 illustrates an exemplary flow diagram for the receipt of input data for the Improved Weight Distribution Sensory Device with Integrated Controls 100, shown generally at 806. The process begins from step 804 of FIG. 8. The process then progresses to step 1202 where pressure sensor data is received. Pressure sensor data may be from either the Pressure Sensors 310$a$, 310$b$ to 310$q$ or Bottom Pressure Sensors 502$a$, 502$b$ to 502$n$. Then, at step 1204, control data is received. Control data may be provided from the Control Sensors 308$a$, 308$b$ to 308$m$. Although not illustrated, acceleration data from the Accelerometer 608 may also be received. The process then concludes by progressing to step 808 of FIG. 8.

Figure 13:
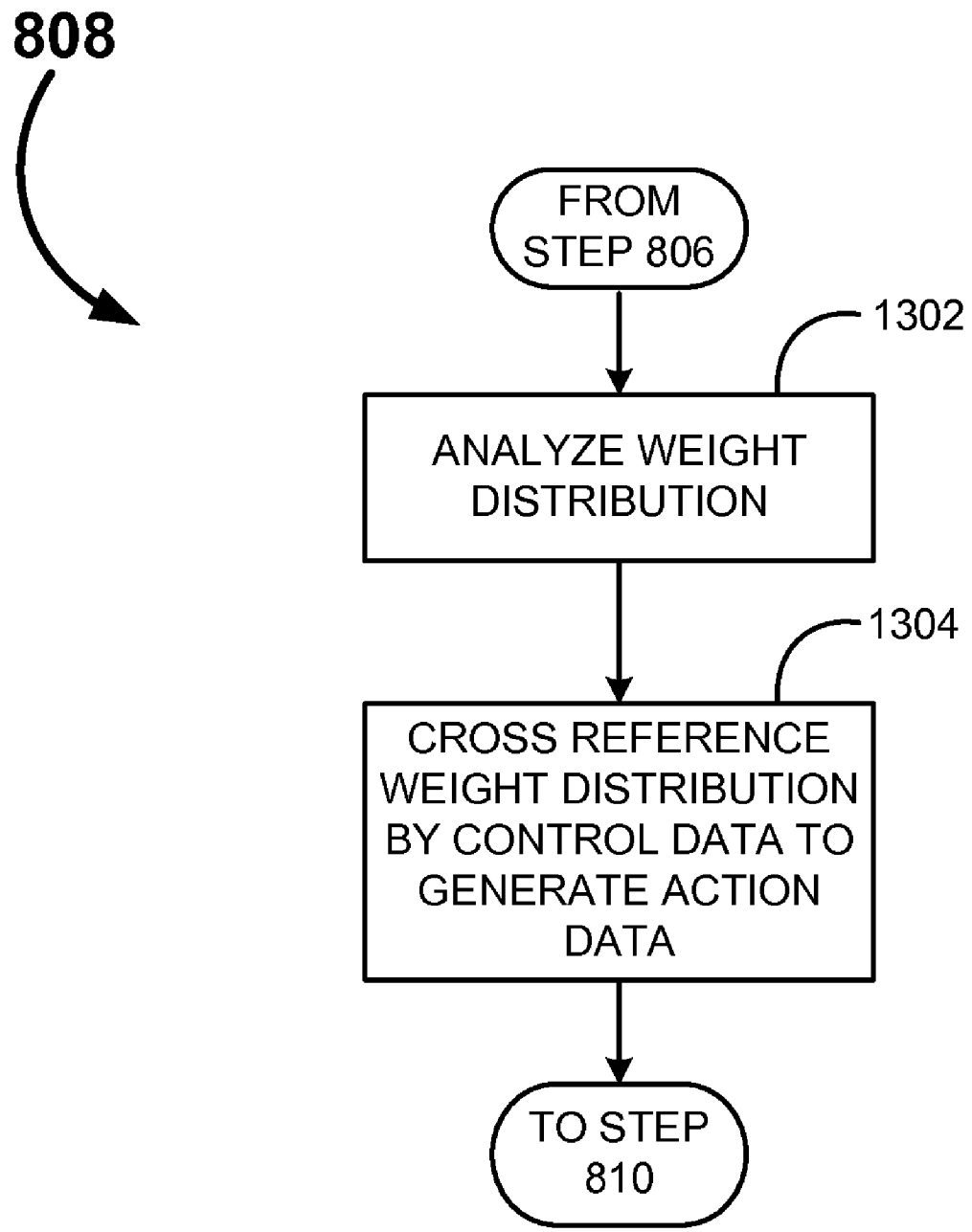
FIG. 13 illustrates an exemplary flow diagram for data processing for the improved weight distribution sensory device with integrated controls in accordance with an embodiment of the present invention.

FIG. 13 illustrates an exemplary flow diagram for data processing for the Improved Weight Distribution Sensory Device with Integrated Controls 100, shown generally at 808. The process begins from step 806 of FIG. 8. The process then progresses to step 1302 where the weight distribution is analyzed. Weight distribution analysis includes summing the perceived force on all pressure sensors to generate a total weight. Then the center of balance may be determined by comparing the perceived force upon each pressure sensor divided by the total weight.

The process then progresses to step 1304 where the weight distribution is cross referenced by the control data, in light of the activity the user is engaged in, to generate action data. Thus, for example, a shift in the user's center of gravity (weight distribution) plus a sweeping motion of her foot over the sensors may be analyzed as a pass of the ball in a soccer game. The process then concludes by progressing to step 810 of FIG. 8.

Figure 14:
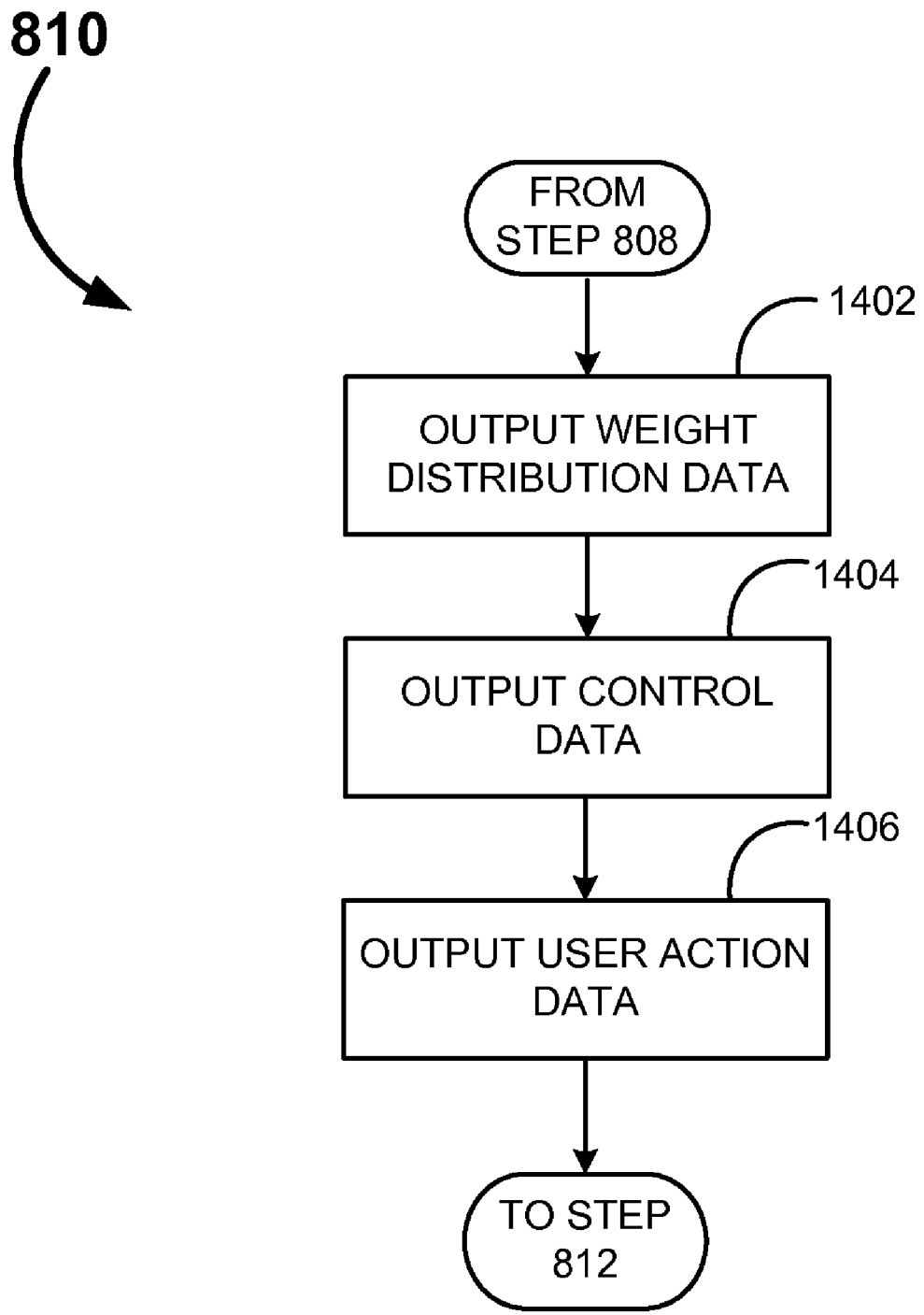
FIG. 14 illustrates an exemplary flow diagram for the output of processed data for the improved weight distribution sensory device with integrated controls in accordance with an embodiment of the present invention.

FIG. 14 illustrates an exemplary flow diagram for the output of processed data for the Improved Weight Distribution Sensory Device with Integrated Controls 100, shown generally at 810. The process begins from step 808 of FIG. 8. The process then progresses to step 1402 where weight distribution data is output. Likewise, control data may be output at step 1404 and user action data may be output at step 1406. The process then concludes by progressing to step 812 of FIG. 8.

In sum, systems and methods for an improved weight distribution sensory device with integrated controls is provided. While the disclosed weight distribution sensory device has been discussed for use with a gaming system, it is also understood that the present weight distribution sensory device has beneficial use in a wide range of training, exercise and therapy applications. For example, such a weight distribution sensory device may be useful in rehabilitating stroke victims in balance activities.

While this invention has been described in terms of several preferred embodiments, there are alterations, modifications, permutations, and substitute equivalents, which fall within the scope of this invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. An improved weight distribution sensory system, useful in conjunction with a user, the improved weight distribution sensory system comprising:
    a chassis configured to support the user;
    more than one pressure sensors configured to couple to the chassis, wherein the more than one pressure sensors generates pressure data regarding the compression force from the weight of the user on the chassis;
    one or more control sensors configured to couple to the chassis, wherein the one or more control sensors generates control data when manipulated by the user;
    a processor configured to receive the pressure data and the control data, wherein the processor generates a total weight of the user and a weight distribution of the user from the pressure data, and wherein the processor generates action data for the user by analyzing the weight distribution and the control data in order to map weight distribution and the control data to preset values according to an activity the user is engaged in; and
    an outputter configured to couple to the processor and a downstream system, wherein the outputter outputs the total weight, the weight distribution, the control data, and the action data to the downstream system.

2. The improved weight distribution sensory system of claim 1, further comprising an accelerometer configured to measure accelerations in the chassis.

3. The improved weight distribution sensory system of claim 2, wherein the processor further cross references the measured accelerations in the chassis when generating the action data.

4. The improved weight distribution sensory system of claim 1, wherein the one or more control sensors are located on a forward dorsal portion of the chassis.

5. The improved weight distribution sensory system of claim 4, wherein the one or more control sensors includes at least one proximity sensor.

6. The improved weight distribution sensory system of claim 5, wherein the at least one proximity sensor senses proximity in a narrow band above the sensor along the y-axis.

7. The improved weight distribution sensory system of claim 6, wherein the at least one proximity sensor range is configurable.

8. The improved weight distribution sensory system of claim 5, wherein the at least one proximity sensor includes an array of proximity sensors.

9. The improved weight distribution sensory system of claim 8, wherein the array of proximity sensors is configured to track motion of the user.

10. The improved weight distribution sensory system of claim 1, wherein the downstream system is a computer system.

11. The improved weight distribution sensory system of claim 1, wherein the downstream system is a game console system.

12. A method for generating action data for a user, useful in conjunction with an improved weight distribution sensory system, the method comprising:
    generating pressure data using more than one pressure sensors which are compressed by the weight of the user on the improved weight distribution sensory system;
    generating control data using one or more control sensors which are manipulated by the user;
    determining a total weight of the user by summing the pressure data from each of the more than one pressure sensors;
    generating a weight distribution of the user by analyzing the pressure data from each of the more than one pressure sensors;
    creating action data, using a processor, for the user by analyzing the weight distribution and the control data in order to map weight distribution and the control data to preset values according to an activity the user is engaged in; and
    outputting the action data to a downstream system.

13. The method of claim 12, further comprising measuring accelerations in the improved weight distribution sensory system.

14. The method of claim 13, wherein the creating action data for the user further cross references the measured accelerations in the improved weight distribution sensory system with the weight distribution and the control data.

15. The method of claim 12, wherein the one or more control sensors are located on a forward dorsal portion of the improved weight distribution sensory system.

16. The method of claim 15, wherein the one or more control sensors includes at least one proximity sensor.

17. The method of claim 16, wherein the at least one proximity sensor includes an array of proximity sensors.

18. The method of claim 17, further comprising tracking motion of the user utilizing the array of proximity sensors track motion of the user.

19. The method of claim 12, wherein the downstream system is a computer system.

20. The method of claim 12, wherein the downstream system is a game console system.

* * * * *